United States Patent [19]

Bader et al.

[11] 4,225,705

[45] Sep. 30, 1980

[54] PROCESS FOR SYNTHESIZING THIACYANINE DYES

[76] Inventors: Henry Bader, Newton Center; John W. Sparks, Boston, both of Mass.

[21] Appl. No.: 36,283

[22] Filed: May 7, 1979

[51] Int. Cl.$^3$ .......................................... C07D 417/06
[52] U.S. Cl. .................................... 542/452; 548/152
[58] Field of Search ..................... 260/304 B; 542/452

[56] References Cited

U.S. PATENT DOCUMENTS

| | | | |
|---|---|---|---|
| 3,149,105 | 9/1964 | Larive et al. | 542/452 |
| 4,028,353 | 6/1977 | Borror | 542/452 |

FOREIGN PATENT DOCUMENTS 1445870  8/1976  United Kingdom ..................... 542/452

OTHER PUBLICATIONS

Hamer, The Cyanine Dyes and Related Compounds, Interscience, N.Y., N.Y., 1964, pp. 46, 47, 58, 59.

*Primary Examiner*—Arthur P. Demers
*Attorney, Agent, or Firm*—Gaetano D. Maccarone

[57] ABSTRACT

There is described a process for synthesizing a thiacyanine dye wherein a 2-halo, 2-alkoxy or 2-aryloxybenzothiazole is alkylated by a strong alkylating agent to form a quaternized benzothiazole which, without being isolated, is condensed with a benzothiazolium betaine in a nonaqueous homogeneous medium. The thiacyanine dye is useful for enhancing the photosensitivity of a blue-sensitive silver halide emulsion.

13 Claims, No Drawings

PROCESS FOR SYNTHESIZING THIACYANINE DYES

BACKGROUND OF THE INVENTION

This application relates generally to a chemical process and, more particularly, to a process for synthesizing a thiacyanine dye.

British Pat. No. 1,445,870, issued Dec. 8, 1976, discloses the incorporation of a particular class of thiacyanine dyes into a silver halide photosensitive emulsion in order to enhance the sensitivity of the emulsion to the blue region of the visible spectrum. The preferred thiacyanine dye is anhydro-5-chloro-3'-ethyl-3-(4-sulfobutyl)-thiacyanine hydroxide

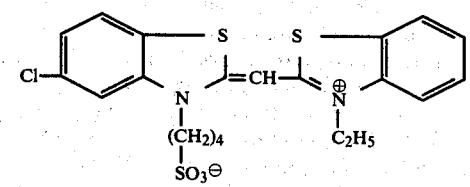

This compound may be prepared by adding 2-ethylthio-3-ethyl benzothiazolium tosylate to a warm solution of 5-chloro-2-methyl-3-(4-sulfobutyl)-benzothiazolium betaine, adding triethylamine and stirring vigorously. The desired product can be recovered from the reaction mixture by filtration, purified and recrystallized. This reaction is not completely satisfactory because ethyl mercaptan is formed as a by product. Ethyl mercaptan is a noxious chemical which boils at 35° C. and the complete elimination of this material from the product is extremely difficult. Accordingly, it would be desirable to have a synthesis for such thiacyanine dyes which would not form an alkyl mercaptan as a by-product. The present invention is drawn to such a synthesis.

SUMMARY OF THE INVENTION

It is therefore the object of the invention to provide a process for synthesizing thiacyanine dyes.

It is another object of the invention to provide such a process where an alkyl mercaptan is not formed as a by-product.

It is a further object to provide a continuous process for synthesizing thiacyanine dyes wherein the intermediate formed is not isolated.

BRIEF SUMMARY OF THE INVENTION

These and other objects and advantages are accomplished in accordance with the invention by providing a process for synthesizing a thiacyanine dye wherein a 2-halo, 2-alkoxy or 2-aryloxybenzothiazole (I) is alkylated by a strong alkylating agent to form a quaternized benzothiazole (II) which, without being isolated, is condensed with a benzothiazolium betaine (III) in a nonaqueous homogenous medium. The process can be illustrated as follows:

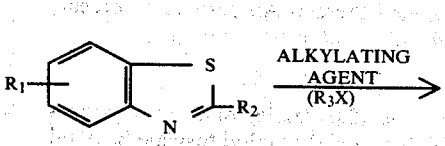

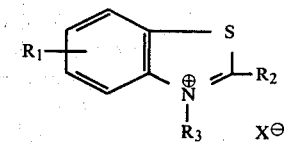

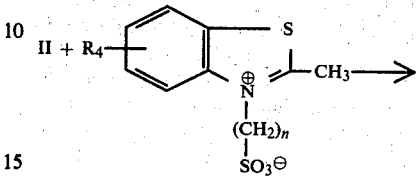

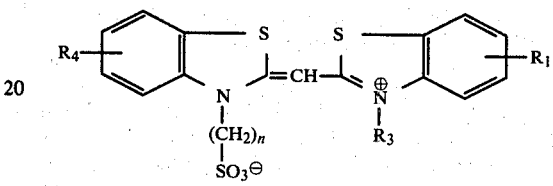

wherein $R_1$ may be hydrogen, halogen or alkyl, alkoxy or haloalkyl having from 1 to 12 carbon atoms; $R_2$ may be halogen, lower alkoxy having from 1 to 6 carbon atoms or aryloxy; $R_3$ may be alkyl having from 1 to 18 carbon atoms or aralkyl; $R_4$ may be hydrogen, halogen or alkyl, alkoxy or haloalkyl having from 1 to 12 carbon atoms; n is an integer of from 1 to 18; and X is an anion.

It would not be expected that the substitution of a benzothiazole containing an alkoxy, aryloxy or halo function in place of the alkylmercapto function present in the reactant used in the prior art process would give the thiacyanine dye in any significant yield since, for example, 2-alkoxybenzothiazoles such as 2-ethoxybenzothiazole and 2-halobenzothiazoles such as 2-chlorobenzothiazole are less nucleophilic than the comparable mercaptobenzothiazole. Thus, attempted quaternization of 2-ethoxybenzothiazole and 2-chlorobenzothiazole with a standard alkylating agent such as ethyl tosylate did not give the desired product even when carried out at an elevated temperature (see Example I). It has been found according to the invention that 2-n-alkoxylbenzothiazoles, 2-halobenzothiazoles and 2-aryloxybenzothiazoles can be quaternized in good yield with strong alkylating agents such as, for example, fluorosulfonates, trifluoromethanesulfonates and oxonium fluoroborates to form quaternary salts which can be condensed with a benzothiazolium betaine to give the desired thiacyanine dye.

The benzothiazolium salts, particularly the 2-chloro and 2-alkoxy salts are unexpectedly reactive compounds and are highly sensitive to nucleophilic agents including water. They are quite unstable in moist air making their isolation and storage difficult. Thus, according to the invention, the quaternized salt (compound II) is not isolated from the reaction medium.

The quaternized salts also have a tendency to undergo solvolysis in the presence of the amine typically used to promote condensation with the betaine and this competes with the desired reaction. Accordingly, aqueous conditions which would be preferred normally because of the typically poor solubility of the betaine in common organic solvents would not be suitable because of the competing hydrolysis of the benzothiazolium salt.

Heterogeneous conditions, i.e., where the benzothiazolium salt is in solution and betaine is not are undesirable because solvolytic degradation will occur while the desired condensation reaction is retarded due to the unavailability of the betaine in solution. Thus, according to the invention there is added to the benzothiazolium salt reaction medium, which comprises an aprotic solvent such as methylene chloride, a condensation agent and then, preferably within a short period of time of minimize solvolysis, a solution of the betaine in a solvent such as will provide a nonaqueous homogeneous reaction medium, for example, trifluoroethanol. In a preferred embodiment of the invention, prior to the addition of the condensation agent, the benzothiazolium salt reaction medium is diluted with a solvent such as ethanol.

DESCRIPTION OF THE PREFERRED EMBODIMENTS

Any suitable 2-halo,2-alkoxy or 2-aryloxybenzothiazoles may be used as the starting material for the synthesis of the desired thiacyanine dye. The suitable alkoxybenzothiazoles have a primary alkoxy group. The 2-isopropoxy benzothiazole can be prepared; however attempted quaternization of this compound resulted in an undesired side reaction. Typical suitable benzothiazoles include, for example, 2-chloro, 2-methoxy, 2-ethoxy, 2-n-propoxy, 2-phenoxy 2-(p-chlorophenoxy),2-(p-methoxyphenoxy) and the like. The preparation of such benzothiazoles is known in the art and accordingly, discussion of such preparation is not required here. The alkylation of the benzothiazoles is carried out in an aprotic solvent which may be an aliphatic or aromatic hydrocarbon or a chlorinated hydrocarbon such as, for example, benzene, toluene, xylene, chloroform, dichloroethane, methylene chloride, ethyl acetate, acetonitrile and tetrahydrofuran. The solvent should be one in which the quaternary salt being formed is stable. Methylene chloride and acetonitrile are preferred because they typically provide higher yields of the quaternized salts; methylene chloride is particularly preferred because of ease of handling and its lower toxicity. The concentration of the benzothiazole in the solution typically is in the range of from about 30% to about 60% by weight. It is preferred to use the higher concentrations within this range since typically, higher yields are obtained at the higher concentration levels.

As described above, a very strong alkylating agent is required in order for the desired quaternization reaction to take place. Typical suitable alkylating agents which may be used in the process include, for example, alkylfluorosulfonates such as ethyl fluorosulfonate, fluoromethanesulfonates such as ethyl trifluoromethanesulfonate and oxonium fluoroborates such as triethyloxonium fluoroborate. Typically, from 1 to 2 equivalents of the alkylating agent to 1 equivalent of the benzothiazole are used; it is preferred to use about 1.1 equivalents of the alkylating agent because it provides the best balance between the yield of the salt and most efficient use of materials.

The quaternization reaction is carried out typically at a temperature in the range of from about 5° C. to reflux from a period of from one to 90 hours. The preferred conditions for the quaternization reaction are a temperature of from about 13° C. to about 18° C. for a period of from about 3 to about 24 hours. Highest yields of the salts are obtained from concentrated solutions at a temperature averaging about 15° C. for a period of about 18 hours.

Because of the difficulties attendant to the isolation and storage of the benzothiazolium salts, as discussed previously, the salts are not isolated and the process of the invention is carried out a continuous sequence. The reaction of the benzothiazolium salt with the benzothiazolium betaine (compound III) is carried out in a nonaqueous homogeneous medium in the presence of a condensation promoting agent. Typically, there is initially added to the reaction mixture from about 1 to about 2 equivalents (based on the weight of the salt assuming total alkylation), preferably 1.5, of a condensation promoting agent which may be a tertiary amine such as triethylamine. Subsequently the benzothiazolium betaine (compound III) is introduced as a solution in a protic solvent such as 2,2,2-trifluorothanol. This solvent is chosen so as to ensure complete homogeneity of the reaction medium. The betaine solution is added to the reaction mixture within a very short period of time after the condensation agent is added to the reaction mixture since the benzothiazolium salts undergo solvolysis easily in the presence of condensation agents. An extended delay in adding the betaine solution leads to a significant drop in yield. Accordingly, it is preferred to add the betaine solution immediately.

In a preferred embodiment, the benzothiazolium salt reaction mixture may be diluted by the addition of a protic solvent prior to the addition of the condensation agent and the betaine solution. This solvent should be one which will form a homogeneous reaction medium. Typical suitable solvents include, for examples, alcohols such as methanol, ethanol and the like. Generally, this solvent may be provided in an amount of from about 1:1 to about 5:1 (vol/vol) of the solvent used in the quaternization reaction.

The condensation reaction is carried out typically for a period of from about 3 to about 18 hours. Typically, higher yields are obtained at the shorter reaction times and accordingly the shorter times are preferred. Good yields of the thiacyanine dye have been obtained with a homogenous reaction medium made up of 5 parts of ethanol, 1 part of methylene chloride and 1.2 parts of trifluoroethanol (by volume) with a reaction time of three hours.

The crude thiacyanine dye can be purified such as by recrystallization or trituration. The thiacyanine dyes synthesized according to the invention are substantially insoluble in many common organic solvents as well as water. However, the dyes are soluble in some combinations of solvents such as methanol-trifluoroethanol. Preferably, purification can be carried out by trituration in a slurry of a solvent such as methanol. Where additional purification is required further treatment of the dye with refluxing acetic acid followed by final trituration with refluxing methanol will provide a substantially pure product.

The invention will now be described in detail with respect to specific preferred embodiments thereof by way of examples, it being understood that these are intended to be illustrative only and the invention is not limited to the materials, conditions, process parameters, etc., which are recited therein. All parts and percentages are by weight unless otherwise recited.

EXAMPLE I

A mixture of 1.7 g (0.01 mole) of 2-ethoxybenzothiazole and 2.2 g (0.01 mole) of ethyl tosylate in 20 ml of N,N-dimethylformamide (dried over 3A molecular sieves) was heated to 130° C. and held at that temperature for 16 hours. Reaction occurred slowly to give a mixture of several products as determined by analysis of the reaction mixture by thin layer chromatography. Only a trace of the desired quaternary salt was present in the reaction mixture.

A mixture of 1.7 g (0.01 mole) of 2-chlorobenzothiazole and 2.2g (0.01 mole) of ethyl tosylate in 20 ml of N, N-dimethylformamide (dried over 3 A molecular sieves) was heated to about 130°-140° C. for 5 hours. Analysis of the reaction mixture by thin layer chromatography showed a complex reaction mixture with only a trace of the desired quaternary salt.

EXAMPLE II

A. PREPARATION OF 2-ETHOXYBENZOTHIAZOLE

Exactly 5.8 g of hexane-wet sodium spheres (0.02 mole) was carefully dissolved in 100 ml of anhydrous ethanol. To the resulting cooled sodium ethoxide solution, stirring at 25° C. under nitrogen, was added a solution of 33.8 g (0.2 mole) of 2-chlorobenzothiazole in 100 ml of ethanol over a seven minute interval. There was a strong exotherm during this addition. The reaction mixture was heated to a reflux over 15 min and held at reflux for one hour. The apparatus was then fitted for downward distillation and the ethanol distilled from the reaction mixture at atmospheric pressure over a period of one hour. The cooled oily residue was dissolved in 50 ml of methylene chloride and rapidly stirred for 10 min with 400 ml of water. The organic layer was separated, dried over anhydrous potassium carbonate and stripped of solvent under vacuum. The crude product was distilled under reduced pressure to give 33.15 g (93%) of analytically pure 2-ethoxybenzothiazole, b.p. 78°-80° C., 0.11mm. (lit b.p. 80°-81°, 0.2 mm.) : UV (MeOH):- $\lambda_{max}$218 nm ($\epsilon$=31,100),$\lambda_{max}$245 nm ($\epsilon$=7,800),$\lambda_{max}$277 nm ($\epsilon$=1,100),$\lambda_{max}$287 nm ($\epsilon$=1,060).

B. PREPARATION OF 2-METHYL-3-(4'-SULFOBUTYL)-5-CHLOROBENZOTHIAZOLIUM BETAINE

Exactly 91.8 g (0.50 mole) of 5-chloro-2-methylbenzothiazole, 71.5 g (0.525 mole) of 1,4-butanesultone and 100 ml of tetrahydrothiophene-1, 1-dioxide were stirred in a 250 ml flask equipped with reflux condenser and nitrogen atmosphere. The mixture was heated over a two hour period to 160°±2° C. and kept at that temperature for 20 hrs. After cooling, the thick slurry was filtered and the solid was stirred for 15 min at 25° C. with 600 ml off acetone. Filtration followed by acetone rinsing until the filtrate was colorless and drying at 60° C. under vacuum gave 121.8 g of the betaine (76% yield) UV (MeOH)$\lambda_{max}$225 nm ($\epsilon$=26,300),$\lambda_{max}$270 nm ($\epsilon$=5,240),$\lambda_{max}$295 nm ($\epsilon$=4,230). The purity of the betaine product, a light tan solid was adequate for its use in the condensation step.

C. QUATERNIZATION AND CONDENSATION

To a 500 ml flask equipped with magnetic stirrer were added 8.95 g. (0.05 mole) of 2-ethoxybenzothiazole, 25 ml of methylene chloride and 7.04 g (0.055 mole) of ethyl fluorosulfonate. After initial stirring, the reaction was allowed to stand at 13° C. without agitation for 22 hours. The stirred solution was then diluted with 250 ml of ethanol. Triethylamine, (11 ml) was then added to the solution, now at 25° C., immediately followed by the addition of a solution of 16 g betaine in 62 ml 2,2,2-trifluoroethanol. The dye started forming immediately and began precipitating during the first five minutes. The reaction mixture was stirred at room temperature for three hours, filtered, washed with 50 ml of ethanol and dried in vacuo for 12 hours at 60° C. to give 17.7 g of the dye. The dye contained a significant amount of a magenta colored impurity.

D. PURIFICATION

1. The crude dye (4.5 g) was rapidly stirred in 120 ml of refluxing acetic acid for two hours. The trituration mixture was cooled to 25° C. over ½ hour, filtered and washed with two 15 ml portions of methanol. The solid was dried at 70° C. in vacuo for 14 hours to give 4.65 g of the thiacyanine dye,$\lambda_{max}$432 nm ($\epsilon$=85,500), which was shown by thermogravimetric analysis to contain 2.9% low temperature volatiles and 6.1% high temperature volatiles. An absorption spectrum of a solution of the dye, when compared with that of a standard known not to contain any impurity, showed no megenta colored impurity at 565 nm.

2. The above product (1.5 g) was rapidly stirred in 30 ml of refluxing methanol for two hours. The trituration mixture was cooled to 25° C. over 30 minutes before filtering and washing with 10 ml of methanol. The solid was dried at 70° C. in vacuo for 14 hours to give 1.44 g of product for a nearly quantitative recovery over the two purification steps. The overall yield of product, based on 2-ethoxybenzothiazole, was 74% of theory. The final dye,$\lambda_{max}$432 nm (68 =85,700), was analyzed by thermogravimetric analysis and found to contain 9.32% low temperature volatiles and an absorption spectrum of a solution of the dye, compared to that of a standard, indicated no magenta impurity at 565 nm.

EXAMPLE III

2-Ethoxybenzothiazole, 8.95 g, was quaternizd and condensed as in Example II, part C, except that the stirred solution of 2-ethoxybenzothiazole, methylene chloride (25 ml) and ethyl fluorosulfonate (7.04 g) was diluted with 250 ml of n-butanol instead of ethanol. The yield was 18.3 g (76% of theory) of anhydro-5-chloro-3'-ethyl-3-(4-sulfobutyl) thiacyanine hydroxide, containing a significant amount of magenta-colored impurity. The crude dye (4.5 g) was purified as in Example II (D1) above to give 4.44 g of the dye,$\lambda_{max}$432 nm ($\epsilon$=81,300), containing 3.9% low temperature volatiles and 5.7% high temperature volatiles. The absorption spectrum of a solution of the dye showed trace amounts of magenta impurity absorbing at 565 nm. Exactly 1.5 g of that dye was rapidly stirred in 30 ml of refluxing methanol for two hours. Trituration, filtering, washing and drying as in Example II (D2) gave 1.44 g of the product. The overall yield, based on 2-ethoxybenzothiazole, was 73%. The final dye,$\lambda_{max}$432 nm ($\epsilon$=79,680), was analyzed by thermogravimetric analysis and found to contain 9.32% low temperature volatiles. An absorption spectrum of a solution of the dye showed no magenta impurity absorbing at 565 nm.

EXAMPLE IV

Freshly distilled 2-chlorobenzothiazole (1.7 g, 0.01 mole) was stirred with 1.41 g (0.011 mole) of ethyl fluorosulfonate in 5 ml of methylene chloride at reflux for 16 hr. After being cooled to 25° C., the mixture was diluted with 50 ml of ethanol and 3.5 ml (0.025 mole) of triethylamine were added. Immediately 3.2 g (0.01 mole) of betaine in 12 ml of 2,2,2-trifluoroethanol were added and the mixture stirred at 25° C. for 3 hours. The yield of crude anhydro 5-chloro-3'-ethyl-3-(4-sulfobutyl) thiacyanine hydroxide was 3.1 g (64% of theory).

EXAMPLES V–VIII

Experiments were conducted to compare the ethyl fluorosulfonate and triethyloxonium fluoroborate alkylating agents and various reaction parameters. The syntheses were carried out using 2-ethoxybenzothiazole and 5-chloro-2-methyl-3-(4-sulfobutyl) benzothiazolium betaine with triethylamine as the condensation agent. The quaternization reaction was carried out in methylene chloride at room temperature, the quaternization salt reaction mixture was diluted with ethanol prior to adding the triethylamine and the betaine was dissolved in 2,2,2,-trifluoro-ethanol. The results are shown in Table I.

TABLE I

| Example | Alkylating Agent | Quaternization Time (hours) | Triethylamine (Equivalents) | Condensation Time (Hours) | Yield of Dye (%) |
|---|---|---|---|---|---|
| V | Fluorosulfonate | 24 | 1.3 | 19 | 52 |
| VI | Fluorosulfonate | 18 | 1.5 | 3 | 60 |
| VII | Fluoroborate | 2.5 | 1.3 | 18 | 53 |
| VIII | Fluoroborate | 2.5 | 1.5 | 3 | 55 |

EXAMPLES IX–XI

Experiments were conducted to study the fluorosulfonate quaternization with respect to time and temperature of the quaternization step. The quaternization step was carried out with double the reactant concentrations used in Examples V–VIII. All condensations were carried out with 1.5 equivalents of triethylamine for 3 hours. All other variables were identical to those used in Examples V–VIII. The results are shown in Table II.

TABLE II

| EXAMPLE | ALKYLATING AGENT (EQUIV.) | QUATERNIZATION TIME (HOURS) | TEMP (°C.) | YIELD OF DYE (%) |
|---|---|---|---|---|
| IX | Fluorosulfonate (1.1) | 18 | 15 | 78 |
| X | Fluorosulfonate (1.1) | 42 | 17 | 67 |
| XI | Fluorosulfonate (1.1) | 64 | 5 | 76 |

Although the invention has been described in detail with respect to various embodiments thereof, these are intended to be illustrative only and not limiting of the invention but rather those skilled in the art will recognize that modifications and variations may be made therein which are within the spirit of the invention and the scope of the appended claims.

What is claimed is:

1. A process for preparing a thiacyanine dye comprising the steps of
   (a) reacting a benzothiazole represented by the formula

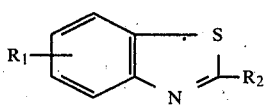

wherein $R_1$ may be hydrogen, halogen, or alkyl, alkoxy or haloalkyl having from 1 to 12 carbon atoms; and $R_2$ may be halogen, alkoxy having from 1 to 6 carbon atoms or aryloxy dissolved in an aprotic solvent with an alkylating agent, selected from the group consisting of alkyl fluorosulfonates, alkyl trifluoromethanesulfonates and trialkyloxonium fluoroborates, wherein each alkyl group of said alkylating agents has from 1 to 18 carbon atoms, to form a quaternized benzothiazole and, without isolating said quaternized benzothiazole;
   (b) adding a condensation agent to the quaternized benzothiazole reaction medium; and
   (c) adding to said reaction medium a solution of a benzothiazolium betaine represented by the formula

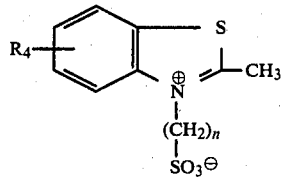

wherein $R_4$ may be hydrogen, halogen or alkyl, alkoxy or haloalkyl having from 1 to 12 carbon atoms and n is an integer of from 1 to 18 in a first protic solvent wherein a homogeneous reaction medium is formed and reacting said quaternized benzothiazole and said benzothiazolium betaine to form a thiacyanine dye represented by the formula

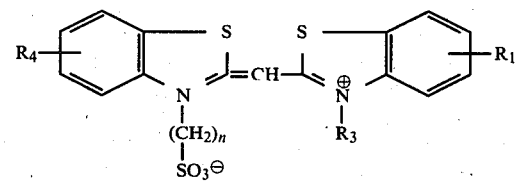

wherein $R_3$ is alkyl having from 1 to 18 carbon atoms.

2. The process as defined in claim 1 wherein said first protic solvent is, 2,2,2-trifluoroethanol.

3. The process as defined in claim 1 wherein said alkylating agent is ethyl fluorosulfonate.

4. The process as defined in claim 1 wherein said aprotic solvent is a member of the group consisting of methylene chloride, chloroform, acetonitrile, ethyl acetate and tetrahydrofuran.

5. The process as defined in claim 4 wherein said aprotic solvent is methylene chloride.

6. The process as defined in claim 5 wherein said first protic solvent is 2,2,2 trifluorethanol and said condensation agent is an organic tertiary amine.

7. The process as defined in claim 6 wherein said condensation agent is triethylamine.

8. The process as defined in claim 1 and further including, prior to step (b), diluting said quaternized benzothiazole reaction medium with a second protic solvent.

9. The process as defined in claim 8 wherein said second protic solvent is an alcohol.

10. The process as defined in claim 9 wherein said aprotic solvent is methylene chloride, said first protic solvent is 2,2,2-trifluoroethanol and said second protic solvent is ethanol.

11. The process as defined in claim 1 wherein step (a) is carried out at a temperature of from about 13° C. to about 18° C. for a period of from about 3 to about 24 hours.

12. The process as defined in claim 11 wherein said quaternized benzothiazole and said benzothiazolium betaine are reacted for a period of from about 3 to about 18 hours.

13. A process for preparing anhydro-5-chloro-3'-ethyl-3-(4-sulfobutyl) thiacyanine hydroxide which comprises quaternizing 2-ethoxybenzothiazole with ethyl fluorosulfonate in methylene chloride to form 2-ethoxy-3-ethylbenzothiazolium fluorosulfonate, diluting the reaction medium with a solvent selected from the group consisting of n-butanol and ethanol and condensing said 2-ethoxy-3-ethylbenzothiazolium fluorosulfonate with a solution of 2-methyl-3-(4-sulfobutyl)-5-chlorobenzothiazolium betaine in 2,2,2-trifluoroethanol in the presence of triethylamine.

* * * * *

UNITED STATES PATENT AND TRADEMARK OFFICE
CERTIFICATE OF CORRECTION

PATENT NO. : 4,225,705

DATED : September 30, 1980

INVENTOR(S) : Henry Bader and John W. Sparks

It is certified that error appears in the above-identified patent and that said Letters Patent are hereby corrected as shown below:

On the title page, after "Inventors" and before "Appl. No." insert ---Assignee: Polaroid Corporation, Cambridge, Mass.---.

Column 2, line 46, delete "alkoxylbenzothiazoles" and insert ---alkoxybenzothiazoles---.

Column 4, line 17, delete "trifluorothanol" and insert ---trifluoroethanol---.

Column 5, line 19, delete "0.02" and insert ---0.2---.

Column 5, line 52, delete "off" and insert ---of---.

Column 6, line 21, delete "megenta" and insert ---magenta---.

Column 6, line 31, delete "(68=85,700 )" and insert ---($\epsilon$ = 85,700)---.

Signed and Sealed this

Thirty-first Day of March 1981

[SEAL]

Attest:

RENE D. TEGTMEYER

Attesting Officer

Acting Commissioner of Patents and Trademarks